United States Patent [19]

Terfloth et al.

[11] Patent Number: 5,449,799
[45] Date of Patent: Sep. 12, 1995

[54] COMPOUND FOR DEPOSITING COPPER LAYERS

[76] Inventors: Christian Terfloth, Sülzgürtel 96, D-5000 Koln 41, Germany; Thomas Kruck, Am Wachberg 9, D-5024 Erftstadt-Bliesheim, Germany

[21] Appl. No.: 85,947

[22] Filed: Jul. 6, 1993

[30] Foreign Application Priority Data

Jul. 4, 1992 [DE] Germany .................. 42 22 021.1

[51] Int. Cl.⁶ .................................. C07F 1/08
[52] U.S. Cl. ..................................... 556/112
[58] Field of Search ........................... 556/112

[56] References Cited

U.S. PATENT DOCUMENTS

| 4,915,988 | 4/1990 | Erbil | 556/112X |
| 4,927,670 | 5/1990 | Erbil | 556/112 X |
| 5,306,836 | 4/1994 | Purdy | 556/112 |

FOREIGN PATENT DOCUMENTS

| 0297348B1 | 3/1992 | European Pat. Off. . |
| 41 24 686A1 | 1/1992 | Germany . |

OTHER PUBLICATIONS

Norman, et al., "New OMCVD Precursors For Selective Copper Metalization", Journal de Physique IV, 1:C2-271—C2-279 (1991).

Shin, et al., "Selective Low-Temperature Chemical Vapor Deposition of Copper from (Hexafluoroacetyl-acetonato)copper(I)trimethylphosphine ,(hfa)CuP(Me)₃", Advanced Materials, 3:246-248 (1991).

Ito, et al., "A New Preparation and Some Reactions of Organocopper(I) Isonitrile Complexes", Journal of Organometallic Chemistry, 85:395-401 (1975).

Nast, et al., "Stabile Addukte von Kupfer-(I)-acetylacetonat", Chem Ber., 102:3224-3228 (1969).

Primary Examiner—Paul F. Shaver
Attorney, Agent, or Firm—Banner & Allegretti

[57] ABSTRACT

Described is the deposition of copper-containing layers on substrates by decomposition of organometallic copper compounds containing acetylacetonato or substituted acetylacetonato and isonitrile. The decomposition is preferably carried out in accordance with CVD method.

8 Claims, No Drawings

COMPOUND FOR DEPOSITING COPPER LAYERS

BACKGROUND OF THE INVENTION

1. Field of the Invention

The invention relates to copper compounds and to a process for depositing a copper-containing layer on a substrate.

2. Review of Related Art

It has been known to modify substrates by coating the surfaces thereof in such a manner that the surface will have certain functional properties. For example, electroconductive layers, e.g., conductor paths, can be applied onto substrates.

From EP-0 472 897 A1 (DE-41 24 686 A1) there has been known a process for depositing copper-containing layers on substrates, which process utilizes copper compounds containing cyclopentadienyl or substituted cyclopentadienyl.

J.A.T. NORMAN, ET AL. (*Journal de Physique IV*, Col. C2, suppl. *Journal de Physique II*, Vol. 1, 1991, C2-271) describe the deposition of copper-containing layers by means of hexafluoroacetylacetonato (trimethylvinylsilane) copper (I) (RCuTMVS). The authors describe a decomposition mechanism including a disproportionation according to the following mechanism:

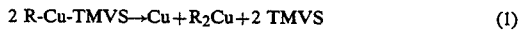

$$2\ R\text{-}Cu\text{-}TMVS \rightarrow Cu + R_2Cu + 2\ TMVS \qquad (1)$$

This composition mechanism (1) has been confirmed by other authors also for other compounds of the type R-Cu-L', for example by M. J. HAMPDEN-SMITH ET AL. (Advanced Materials, 1991, Vol. 3, page 246f) for compounds wherein L' represents trialkylphosphane, inter alia. The decomposition mechanism (1) has the inherent drawback that the maximum copper yield attainable for the layer is just 50%, i.e. at least half of the amount of the starting compound will be lost.

SUMMARY OF THE INVENTION

It is the object of the present invention to provide new copper compounds which are usable in the process according to the invention and of which the total amount of copper is available for the layer to be produced.

It is a further object of the present invention to provide a process for depositing a copper-containing layer on a substrate.

Said objects are attained by the process according to the invention and the copper compounds represented by the general formula (I) that can be employed in said process.

Thus, in a first embodiment the invention relates to copper compounds represented by the general formula (I)

$$R\text{-}Cu\text{-}L_n \qquad (I)$$

wherein R represents acetylacetonato, substituted acetylacetonato of the general formula $X^1C(O)CX^2C(O)X^3$, pentane-2-keto-4-ketiminato, substituted β-ketiminato of the general formula $X^1C(O)CX^2C(NX^4)X^3$, 2,4-pentanediketiminato or substituted β-diketiminato of the general formula $X^1C(NX^4)CX^2C(NX^5)X^3$, wherein $X^1$ and $X^3$ may be the same or different and represent a linear or branched alkyl having from 1 to 5 carbon atoms, halogen-substituted linear or branched alkyl having from 1 to 7 carbon atoms, aryl, substituted phenyl or organylsilyl, and $X^2$, $X^4$ and $X^5$ may be the same or different and represent hydrogen, halogen, linear or branched alkyl having from 1 to 5 carbon atoms, halogen-substituted linear or branched alkyl having from 1 to 7 carbon atoms, aryl or organylsilyl;

L represents ($C_1$–$C_{10}$-alkyl) isonitrile, halogen-substituted linear or branched alkylisonitrile having from 1 to 5 carbon atoms, arylisonitrile or organylsilylisonitrile; and n represents the number of complex-bonded groups L in the compound (I), where n may assume values from 1 to 4.

Preferred compounds are those wherein $X^1$ and $X^3$ represent alkyl which optionally is substituted with halogen, and especially fluoro-substituted, said alkyl having been selected from methyl, ethyl, propyl, butyl, pentyl, isopropyl, t-butyl, and neopentyl; trifluoromethyl; nonafluorobutyl; phenyl; tolyl; trimethylsilyl or triethylsilyl; and $X^2$, $X^4$ and $X^5$ represent hydrogen; chlorine; fluorine; alkyl which optionally is substituted with halogen, and especially fluoro-substituted, said alkyl having been selected from methyl, ethyl, propyl, butyl, pentyl and isopropyl; trifluoromethyl; triethylsilyl; phenyl; substituted phenyl; or tolyl.

L preferably represents ($C_1$–$C_6$-alkyl) isonitrile, which may optionally be fluoro-substituted. It is particularly preferred that L represents methylisonitrile, t-butylisonitrile, neopentylisonitrile, cylclohexylisonitrile, phenylisonitrile or trimethylsilylisonitrile.

In preferred compounds of the formula (I) n has the values of 1 or 2. Especially preferred compounds are those wherein R represents trifluoromethylacetylacetonato; hexafluoroacetylacetonato; 5,5,6,6,7,7,8,8,8-nonafluorooctane-2,4-dionato; 5,5-dimethylhexane-2,4-dionato; 2,2,6,6-tetramethylheptane-3,5-dionato; benzoylacetonato; pentane-2-imine-4-ketonato; pentane-2-(N-ethyl)imine-4-ketonato; pentane-2-(N-isopropyl)imine-4-ketonato; pentane-2,4-diketiminato; pentane-2,4-(N-ethyl, N'-ethyl)-diketiminato.

Another embodiment of the present invention consists of depositing a copper-containing layer on a substrate by adding the compounds of the general formula (I).

Because compounds of the general. formula (I) where L is tert-butylisonitrile or phenylisonitrile when n is 2 and R is acetoacetonato are known in the prior art, applicants do not claim these compounds. However, that these compounds would be useful in the method claimed herein for depositing copper-containing layers on a substrate was not known or suggested in the art, and therefore, these compounds are contemplated in the method of this invention which consists of depositing a copper-containing layer on a substrate by adding the compounds of the general formula (I).

DETAILED DESCRIPTION OF THE INVENTION

The preparation of the compounds represented by the general formula (I) is described hereinbelow. The preparation of compounds of the general formula (I) may be accomplished via different synthesis routes. A simple one-step synthesis for the preparation of Acac-Cu-(CN-t-Bu)₂ from acetylacetone, copper (I) oxide and t-BuNC under a nitrogen atmosphere is described by T. SAEGUSA and Y. ITO (*J. Organometallic Chem.*, 1975, Vol. 85, page 359). Other general compounds of type R-Cu-L$_2$ wherein R represents trifluoromethylacetylacetonato or hexafluoroacetylacetonato can be prepared using substituted acetylacetonates and/or isonitriles L.

Compounds of the type R-Cu-L$_1$ are conveniently prepare by a metatheses reaction between a compound of the type R-alkali metal or R-thallium and a compound of the type L-Cu-halogen, especially L-Cu-Cl, in a solvent such as tetrahydrofuran. After the filtration of the precipitate of alkali metal or thallium halide, respectively, the compound of the type R-Cu-L$_1$ is recovered upon removing the solvent by distillation under reduced pressure.

One general possibility of preparing the compounds of the type R-Cu-L$_2$ or R-Cu-L$_3$ is the reaction of compounds of the type R-Cu-L$_1$ with the appropriate molar amounts of L in a solvent such as tetrahydrofuran. After the solvent has been removed under reduced pressure, the compound is recovered.

Alternatively, compounds of the type R-Cu-L$_1$ may be prepared from R-Cu-L$_2$ by evaporating the R-Cu-L$_2$ compound. The resulting gas or vapor phase will contain the desired R-Cu-L$_1$ species, and it may be used directly for deposition from the gas phase as described below. This alternative is preferred when the stability of the copper compound increases with increasing n, so that the species in storage or transport is the more stable species. The coordination number (i.e., ligancy) is in particular influenced by the specific residue R.

To achieve the deposition of a copper-containing layer, the artisan may utilize the deposition from the gaseous or vapor phase. It will be self-evident to an artisan that not only individual compounds of the formula (I), but also mixtures of such compounds may be employed.

If the deposition is made from a condensed phase, the compound of the formula (I), in the neat state or dissolved in a solvent, is placed on the substrate and then decomposed. Usable solvents include polar or non-polar aprotic organic solvents which optionally may exhibit coordinative properties. Suitable solvents are, for example, hydrocarbons such as pentane, aromatic hydrocarbons such as beneze or ethers such as tetrahydrofuran.

Any suitable known method may be employed for applying the respective starting compound to the substrate. The substrate, for example, may be immersed in the compound or in a suitable solution thereof, or the starting compound or a suitable solution thereof may be spread on the substrate, or the compound or a suitable solution thereof may be sprayed onto the substrate, which latter method is preferred. Using this embodiment of the process according to the invention, i.e. applying the starting compound (or an appropriate mixture of starting compounds) from a condensed phase, even large areas may be coated very fast. Then the starting compound applied onto the substrate is subjected to decomposition in order to deposit a copper-containing layer, optionally under reduced pressure. In a preferred mode the decomposition is conducted thermally.

A thermal decomposition may be effected by introducing the substrate coated with a starting compound into an appropriately heated chamber, or by heating the substrate prior to, during and/or after the application of the starting compound at the pre-determined temperature range.

The thermal decomposition may also be radiation-induced, for example using a laser which emits in the spectral UV range, infrared range or visible range and causes the carrier and/or substrate to be heated. If so desired, the decomposition may be by photolysis. The photolytic decomposition may be effected by means of a laser operated at the appropriate wavelength or by means of UV lamp. The decomposition may also be a plasma-induced decomposition, for which purpose the various known processes are suitable. For example, a thermal plasma process may be employed, such as an arc plasma or plasma jet. In this case, the pressure usually is between 10 mbar and ambient pressure. Also well suitable, more specifically, are low pressure plasma processes, e.g. direct current plasma processes, glow discharge plasma processes, and alternating current plasma processes, e.g. low frequency, medium frequency, high frequency plasma processes and microwave plasma processes. The operating pressures usually are below 10 mbar, for example pressure of between $10^{-2}$ and 1 mbar. The plasma-induced decomposition in a glow discharge plasma is carried out in known plasma reactors. Usable are, for example, tube, tunnel, parallel plate and corona discharge reactors. Since the decomposition in a plasma may be carried out at low temperatures, if so desired, the decomposition in a plasma is well suited for coating substrates which possess a relatively low thermal stability, for example for coating plastics. The artisan may control the form in which the copper is present in the layer by way of an addition of a reactive gas.

Another embodiment of the process according to the invention pertains to the decomposition of the starting compound in the gaseous or vapor state. The vapor phase contains amounts of condensed starting compound in a very fine distribution, in addition to the amounts of the starting compound present in the gaseous state. The vapor deposition or a deposition from the gas phase, respectively, allows a deposition of particularly well-adhering uniform thin layers. The pressure in the gas or vapor phase may be higher or lower. For example, a pressure may be utilized which corresponds to the vapor pressure at the working temperature of the starting compound employed. On the other hand, the total pressure may be higher as well, up to ambient pressure. It is expedient to employ a reduced pressure, for example from $10^{-3}$ to 100 mbar, and preferably from 0.1 to 10 mbar.

The decomposition of the starting compound in the gas or vapor phase, respectively, is expediently carried out in accordance with a CVD (Chemical Vapor Deposition) method.

The basic mode of operation for coating substrates using CVD methods and suitable equipment therefor have been known. EP-A 297 348 and EP 0 472 897 A1 provide the artisan with ample information on how a CVD process is to be carried out and which devices are usable.

The decomposition from the gas or vapor phase is conveniently carried out in a pressure-proof evacuated device. The substrate is placed in said device. An atmosphere including the copper-containing compound is generated under reduced pressure. If so desired, an inert gas or a reactive gas may be present in the gas space of the device.

In a preferred variant, first only the substrate is introduced into the pressure-proof device, and the starting compound which is already available in the form of a gas or vapor is continuously or intermittently introduced into said device through a separate conduit. A carrier gas may also be used here. Converting the starting compound into the gas or vapor phase may be promoted by heating and, if desired, by adding a carrier gas.

According to know methods the decomposition is effected thermally, by the action of a plasma and/or photolytically.

The thermal decomposition from the gas or vapor phase is usually carried out by maintaining the walls of the device at a temperature which is about from 10° C. to 30° C. above the evaporation temperature of the starting compound and heating the substrate at a temperature at which the desired copper-containing layer is deposited on the substrate. The required minimum temperature for each compound used may be readily determined by means of simple orienting tests. Usually the temperature at which the substrate is heated is in excess of about 80° C.

Since the thermal CVD process is conventionally carried out at subatmospheric pressure, it is a matter-of-course for the artisan to provide pressure-proof equipment like that used in vacuum technique. The apparatus desirably includes heatable gas conduits for the starting compound and/or the insert gas, gas inlet and outlet ports provided with shutoff valves, optionally ports for introducing a reactive gas, and devices for measuring the temperature. Further required are means for heating the substrate, a pump suitable for generating the desired subatmospheric pressure, a pressure-measuring and -controlling unit and so on. In the case of employing a radiation energy-induced CVD process there must also be present a radiation source emitting a radiation within the region of visible light, the infrared or the ultraviolet region. Especially suitable are appropriate laser radiation energy sources. The substrate may be heated by means of the radiation energy. In the case of employing a plasma-supported CVD process there must still necessarily be present a plasma source capable of generating, for example, high-frequency or microwave plasmas.

The thickness of the copper-containing layers to be produced according to the present process substantially depends on the partial pressure, on the period of time during which the deposition is carried out, and on the deposition temperature.

The morphology of the copper-containing layers to be produced according to the present process substantially depends on the partial pressure, on the kind and composition of the process gases employed and on the substrate.

More or less thin layers may be generated, for example layers having a thickness of up to 20 $\mu$m, and especially of between 10 nm and 20 $\mu$m. Depending on which layer thickness is desired, the artisan may determine the parameters necessary for producing a copper-containing layer of a pre-determined thickness and morphology. As has already been mentioned, the decomposition may also be photolytically effected, e.g. by means of a UV lamp or laser operating at a suitable wavelength; the use of a laser will, for example, allow conductor paths to be repaired.

Now, by means of the present invention, the mechanism by which a compound having the general formula $R$-Cu-$L_n$ decomposes can be controlled by selecting the suitable isonitrile. If an L such as t-butylisonitrile is employed, the decomposition mechanism proceeds according to the following scheme:

$$R\text{-}Cu\text{-}CNtBu \rightarrow Cu + RH + HCN + CH_2=C(CH_3)_2 \quad (2)$$

Where the isontrile L is one which can release HCN to form an unsaturated molecule under the conditions of the Cu deposition process, the compound $R$-Cu$L_n$ will decompose via mechanism (2). The isonitrile L of the compound $R$-Cu-$L_n$ which decomposes via mechanism (2) will usually have at least one hydrogen attached to a carbon adjacent to the carbon carrying the NC group. By way of this decomposition mechanism (2), the total amount of Cu in the compound employed may be utilized for the production of a copper-containing layer.

If it is desired, due to particular process-related reasons, to carry out a decomposition proceeding via the mechanism of equation (1) above, then a component having the general formula $R$-Cu-$L_n$ is selected wherein L represents an isonitrile which cannot decay to form both HCN and a molecule containing at least one multiple bond. For a decomposition proceeding according to decomposition mechanism (1), for example, a compound having the general formula (I) may be used wherein L represents neopenylisonitrile.

If the starting compound is decomposed in the absence of an inert gas or reactive gas, then layers are deposited which contain copper essentially in the metallic form, especially so, if the decomposition is carried out as a CVD process.

Layers obtained by a thermal decomposition, especially in a thermal CVD process, which contain copper essentially in the metallic form, will also be deposited upon operation in the presence of an inert gas, for example in the presence of nitrogen, or in the presence of a reducing gas, for example in the presence of hydrogen.

In another embodiment, the decomposition is carried out in an atmosphere of a reactive hydrolyzing and/or oxidizing gas to produce layers which contain copper essentially in the form of copper oxide.

To achieve a deposition of copper-containing layers which contain the copper oxide substantially in the form of copper (I) oxide, the decomposition is carded out particularly in the form of water vapor. To achieve a decomposition of copper-containing layers which contain the copper oxide substantially in the form of copper (II) oxide, the decomposition is carried out in the presence of an atmosphere containing an oxidizing gas, more particularly in the presence of oxygen, ozone or dinitrogen oxide.

The variants mentioned, of course, may be also cardled out via the plasma-supported or radiation-induced procedures.

By means of the process according to the invention there can basically be coated any desired substrate. For example, as the substrates there may be used inorganic materials such as metals, e.g. aluminum, semiconductors, insulators, ceramics, e.g. titanium nitride, glass phases, or organic materials such as organic polymers like polyperfluoroethylene, polyphenylene sulfide or polyimides.

On the analogy of the process described by J.A.T. NORMAN, ET AL. (loc. cit.), the isonitriles according to the invention may be used in etching processes (3) with a reversal of the decomposition reaction (1):

$$R_2Cu + 2L + Cu \rightarrow 2R\text{-}Cu\text{-}L \quad (3)$$

It is further possible to employ substrates which are also used in the manufacture of superconductors, such as carbon, more specifically carbon fibers, silicon carbide, more specifically silicon carbide fibers, or for example, strontium titanate, aluminum oxide or magnesium oxide.

A decomposition of layers containing the copper essentially in the form of metallic copper provides the possibility, for example, to produce electroconductive paths on non-conducting substrates by covering defined areas which are not intended to be coated using a per se known patterning technique. If, on a substrate surface, electroconductive areas are present adjacent to non-conducting areas, then patterned layers containing copper metal can be easily produced by the process according to the invention using compounds having the general formula (I), since the compounds having the formula (I) tend to be preferably deposited on the electroconductive layers. The artisan will be able by means of simple screening tests to determine the minimum temperature necessary for such a regioselective deposition.

In addition, the process according to the invention offers still further options to the artisan. For example, said process is also suitable for a deposition of layers which contain one or more other metal(s) in addition to copper. This embodiment of the process according to the invention is characterized in that one or more different compounds of the other metal(s) and a compound having the general formula (I) are simultaneously used in order to accomplish a deposition of layers containing copper plus one or more other metal(s). For example, layers which are particularly stable to electromigration can be obtained by simultaneously depositing a compound of the general formula (I) and a suitable aluminum compound. Either an inert or a reactive atmosphere may also be used in this embodiment.

One variant providing aluminum-containing layers which are stable to electromigration comprises depositing a layer containing copper metal on an aluminum metal layer which is annealed from about 400° C. to 450° C. in a subsequent step to form an aluminum-copper alloy.

It is of course feasible also to apply other layers one after another or to change the sequence of how to coat a substrate. For example, a titanium nitride layer preventing a metal diffusion in an electric field may first be applied onto a substrate using a known method, e.g. a PVD (Physical Vapor Deposition) or CVD method, followed by the decomposition of a compound having the general formula (I). Alternatively, a layer containing copper dispersed in a polymer or a copper-doped polymer may be deposited by decomposing a mixture of a compound of the general formula (I) and one or more monomers that polymerize to form a polymer or copolymer under conditions of the decomposition reaction.

The process according to the invention offers advantages over known processes. The decomposition already begins to occur at about 80° C. and, hence, can be carried out without imposing stress on the substrate; the decomposition mechanism can be controlled by appropriately selecting the ligand L; and the stability to air of the compounds can be intentionally modified by selecting the number of ligands L, where the reactive compounds are formed only upon evaporation in the CVD process.

EXAMPLES

In the following Examples the solvents used had been previously dried and distilled under a protective gas atmosphere. All process operations were carried out under an inert gas atmosphere.

Example 1

Preparation of tert-butylisonitrile (pentane-2,4-dionato)-copper (I).

a) 1.2 g (4 mmol) of acacTl (acetylacetonatothallium-(I)=pentane-2,4-dionatothallium(I)) were dissolved in 40 ml of THF (tetrahydrofuran). Then 0.73 g (1 mmol) of tetrakis[tert-butylisonitrile($\mu_3$-chloro)copper(I)], dissolved in 30 ml of THF, were dropwise added at room temperature. Colorless TlCl precipitated. After one hour the mixture was filtered over $MgSO_4$. Upon removal of the solvent from the resulting tiltrate a residue of slightly greenish color caused by the presence of traces of oxidation product was recovered. For further purification the product was to be sublimated at 70° C./0.1 mbar. Thereupon the target compound was obtained as a colorless microcrystalline solid.

Yield: 0.2 (0.8 mmol, 20%).

b) The preparation of acac-Cu-(CNtBu)$_2$ which is hardly sensitive to air was carried out on the analogy of the process by SAEGUSA and ITO, loc. cit. The sublimation of 1 g (3.04 mmol) of the colorless compound thus obtained from the molten state at about 70°–80° C./0.1 mbar resulted in a disassociation of one mole of tert-butylisonitrile per acac-Cu-(CNtBu)$_2$ to form colorless tert-butylisonitrile(pentane-2,4-dionato) copper (I) which condensed on the cold finger.

Yield: 0.41 g (1.67 mmol, 55%); m.p. 95° C., dec.p.: 120° C.

Example 2

Preparation of tert-butylisontrile (1,1,1,5,5,5-hexafluoropentane-2,4-dionato) copper (I).

4.1 g ( 10 mmol) of hfacTl [hexafluoroacentylacetonatothallium(I)=1,1,1,5,5,5-hexafluoropentane-2,4-dionato-thallium(I)] were dissolved in 40 ml of THF. A solution of 1.8 g (2.5 mmol) of tetrakis[tert-butylisonitrile($\mu_3$-chloro) copper (I)] in 40 ml of THF was dropwise added within 1 hour. Colorless TlCl precipitated. After one hour the mixture was filtered over $MgSO_4$. Then the flitrate was concentrated to dryness. The title compound could be recovered in an analytically pure state from the crude yellow product by extraction with pentane (five times 20 ml) and then removal of the solvent by distillation. A subsequent sublimation at 55° C./0.1 mbar also quantatively provided the product as a canary microcrystalline solid.

Yield: 2.7 g (7.6 mmol, 76%); m.p.: 52° C.; dec.p: 160°–165° C.

Example 3

Preparation of bis(tert-butylisonitrile) (1,1,1,5,5,5-hexafluoropentane-2,4-dionato) copper (I).

1.67 g (4.72 mmol) of hfac-Cu-CNtBu were dissolved in 50 ml of THF, and 0.53 ml (4.72 retool) of tert-butylisonitrile were dropwise added thereto. In the course thereof the color of the solution changed from intensely yellow to pale yellow. Upon the completion of the addition of tBuNC, stirring of the mixture was continued for another 30 minutes, and then the solvent was stripped off under reduced pressure. The resulting pale yellow air-insensitive product, after drying, could be sublimated in vacuo at 90° C./0.1 mbar for further purification.

Yield: 2.0 g (4.58 mmol, 97%); m.p.: 94°–96° C.; dec.p: 176°–180° C.

Example 4

Preparation of tert-butylisonitrile (1-phenylbutane-1,3-dionato) copper (I).

In one-vessel synthesis, 0.81 g (5 mmol) of benzoylacetone were dissolved in 50 ml of THF, and 3.1 ml (5 mmol) of butyllithium in hexane were added thereto at −78 ° C. with vigorous stirring. Upon completion of the addition the batch was allowed to thaw. To the resulting yellow solution there were added 0.91 g (1.25 mmol) of [t-BuNCCuCl]$_4$. After one hour the solution which had become turbid was filtered over MgSO$_4$; then the flitrate was concentrated to dryness. The crude product was obtained as bright yellow microcrystalline solid. For further purification, organic contaminants were extracted with several portions of pentane at 0° C. until the pentane phase no longer showed any color. The target compound was finally dried under the vacuum of an oil pump.

Yield: 0.98 g (3.19 mmol, 64%); dec.p.: 171°–174° C.

Example 5

Use of hfac-Cu-CNtBu for depositing copper-containing layers.

The reactors employed were either a cold wall stagnation flow reactor (Example 5a) wherein a substrate of 4 cm$^2$ in size was placed on an induction-heated substrate-holder in a direction perpendicular to the precursor and carrier gas flow, or a simple hot wall laminar flow reactor (Example 5b), in the first heating zone of which the precursor was evaporated and in the second heating zone of which the copper deposition was effected.

Example 5a

Use of titanium nitride as a substrate in a cold wall stagnation flow reactor.

a) Use with N$_2$ as a carrier gas:

At an evaporator temperature of about 65 ° C. hfac-Cu-CNtBu was evaporated from the liquid phase and was decomposed at about 270° C. on a degreased TiN-coated piece of Si. The decomposition was terminated after 45 minutes. A copper layer had been deposited on the specimen.

b) Use with forming gas (95% of N$_2$, 5% of H$_2$) as a carrier and reducing gas:

Under the same conditions as in a) a polycrystalline copper layer was produced.

Example 5b

Use of titanium nitride as substrate in a hot wall laminar flow reactor.

The experiment was carried out at a temperature of the evaporator zone of about 75 ° C. and a temperature of the decomposition zone of about 275 ° C. The transportation of matter was effected in the N$_2$ carrier gas stream at a total pressure of about 10 mbar. In the course of one hour it was observed—in addition to the formation of a copper layer on the tube wall—that a titanium nitride-coated Si wafer which had been introduced into the decomposition zone before the beginning of the experiment became coated and that a greenish-yellow compound condensed shortly downstream of the decomposition zone.

This condensate, after the decomposition had been completed, was dissolved in pentane and was transferred into a Schlenk tube. Then the solvent was removed from the yellow pentane phase and the residue was dried in vacuo. By means of IR- and $^1$H-NMR-spectroscopic characterization the resulting yellow solid was unambiguously identified as hfac-Cu-CNtBu. A colorless copper-free coating of hydrocarbons had condensed in the cold trap.

We claim:

1. A compound represented by formula (I)

$$R\text{-Cu-}L_n \qquad (I)$$

wherein R represents acetylacetonato, substituted acetylacetonato of the formula $X^1C(O)CX^2C(O)X^3$, pentane-2-keto-4-ketiminato, substituted $\beta$-ketiminato of the formula $X^1C(O)CX^2C(NX^4)X^3$, 2,4-pentanediketiminato or substituted $\beta$-diketiminato of the formula $X^1C(NX^4)CX^2C(NX^5)X^3$, wherein $X^1$ and $X^3$ may be the same or different and represent a linear or branched alkyl having from 1 to 5 carbon atoms, halogen-substituted linear or branched alkyl having from 1 to 7 carbon atoms, aryl, substituted phenyl or organylsilyl, and $X^2$, $X^4$ and $X^5$ may be the same or different and represent hydrogen, halogen, linear or branched alkyl having from 1 to 5 carbon atoms, halogen substituted linear or branched alkyl having from 1 to 7 carbon atoms, aryl or organosilyl;

L represents (C$_1$–C$_{10}$-alkyl) isonitrile, halogen-substituted linear or branched alkylisonitrile having from 1 to 5 carbon atoms, arylisonitrile, or organosilylisonitrile; and n represents the number of complex-bonded groups L in the compound (I), where n may assume values of from 1 to 4;

except that L is not tert-butylisonitrile or phenyl isonitrile when n is 2 and R is acetylacetonato.

2. The compound according to claim 1, characterized in that $X^1$ and $X^3$ represent alkyl or alkyl substituted with halogen, said alkyl having been selected from the group consisting of methyl, ethyl, propyl, butyl, pentyl, isopropyl, t-butyl, and neopentyl; trifluoromethyl; nonafluorobutyl; phenyl; tolyl; trimethylsilyl; or triethysilyl.

3. The compound according to claim 1, characterized in that $X^2$, $X^4$ and $X^5$ represent hydrogen; chlorine; fluorine; alkyl or alkyl-substituted with halogen, said alkyl being selected from methyl, ethyl, propyl, butyl, pentyl, and isopropyl; trifluoromethyl; triethylesilyl; phenyl; substituted phenyl; or tolyl.

4. The compound according to claim 1, wherein at least one of $X^1$, $X^2$, $X^3$, $X^4$ and $X^5$ represent fluoro-substituted alkyl.

5. The compound according to claim 1, characterized in that L represents (C$_1$–C$_6$-alkyl) isontrile, fluoro-substituted linear or branched alkylisonitrile, phenylisonitrile or tolylisonitrile.

6. The compound according to claim 1, characterized in that L represents methylisonitrile, t-butylisonitrile, neopentylisonitrile, cyclohexylisonitrile, phenylisonitrile, trimethylsilylisonitrile or triethylsilylisonitrile.

7. The compound according to claim 1, characterized in that R represents trifiuoromethylacetylacetonato; hexafluorooctane-2,4-dionato; 5,5-dimethylhexane-2,4-dionato; 2,2,6,6-tetramethylheptane-3,5-dionato; benzoylacetonato; pentane-2-imine-4-ketonato; pentane-2-(N-ethyl)imine-4-ketonato, pentane-2-(N-isopropyl)i- mine-4-ketonato; pentane-2,4-diketiminato; or pentane-2,4-(N-ethyl)diketiminato.

8. The compound according to claim 6, characterized in that R represents trifluoromethylacetylacetonato; hexafluorooctane-2,4-dionato; 5,5-dimethylhexane-2,4-dionato; 2,2,6,6-tetramethylheptane-3,5-dionato; benzoylacetonato; pentane-2-imine-4-ketonato; pentane-2-(N-ethyl)imine-4-ketonato, pentane-2-(N-isopropyl)imine-4-ketonato; pentane-2,4-diketiminato; or pentane-2,4-(N-ethyl,N'-ethyl)diketiminato.

* * * * *

UNITED STATES PATENT AND TRADEMARK OFFICE
CERTIFICATE OF CORRECTION

PATENT NO. : 5,449,799
DATED : September 12, 1995
INVENTOR(S) : Christian Terfloth and Thomas Kruck

*It is certified that an error appears in the above-identified patent and that said Letters Patent is hereby corrected as shown below.*

On the title page, item [54] and Column 1, line 2,
  Delete "Compound" and insert therefor --Compounds--

The title should properly read:

--Compounds for Depositing Copper Layers--

In claim 7, col. 11, line 1, delete "pentane-2,4-(N-ethyl)diketiminato" and insert therefor --pentane-2,4-(N-ethyl,N'-ethyl)diketiminato--

Signed and Sealed this

Fourteenth Day of November, 1995

Attest:

Attesting Officer

BRUCE LEHMAN

Commissioner of Patents and Trademarks